United States Patent [19]

Okada

[11] Patent Number: 5,122,617

[45] Date of Patent: Jun. 16, 1992

[54] TETRACARBOXYLIC ACID DIANHYDRIDES

[75] Inventor: Koji Okada, Ohtsu, Japan

[73] Assignee: Kanegafuchi Kagaku Kogyo Kabushiki Kaisha, Osaka, Japan

[21] Appl. No.: 749,342

[22] Filed: Aug. 23, 1991

[30] Foreign Application Priority Data

Aug. 24, 1990 [JP] Japan .................................. 2-223363
Aug. 24, 1990 [JP] Japan .................................. 2-223364

[51] Int. Cl.[5] .................. C07D 409/00; C07D 307/02
[52] U.S. Cl. ........................................ 549/241; 549/60
[58] Field of Search .................................. 549/60, 241

[56] References Cited

U.S. PATENT DOCUMENTS

| | | | |
|---|---|---|---|
| 3,891,633 | 6/1975 | Berlin et al. | 549/241 |
| 4,490,545 | 12/1984 | Winzenburg et al. | 549/241 |
| 4,571,425 | 2/1986 | Silva | 549/241 |
| 5,003,085 | 3/1991 | Behrend et al. | 549/241 |

*Primary Examiner*—Cecilia Shen
*Attorney, Agent, or Firm*—Armstrong & Kubovcik

[57] ABSTRACT

Tetracarboxylic acid anhydrides represented by the following formulae [IA] and [IB] are provided:

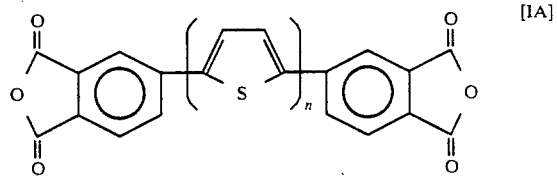

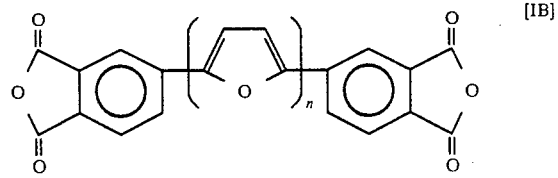

where n is an integer of 1 to 3.

The tetracarboxylic acid anhydrides give polyimides having low thermal expansion, low dielectric constant and low hygroscopicity.

2 Claims, No Drawings

TETRACARBOXYLIC ACID DIANHYDRIDES

BACKGROUND OF THE INVENTION

1. Field of the Invention

The present invention relates to novel acid dianhydrides useful as a raw material for heat-resistant resins such as polyimides.

2. Description of the Prior Art

Because of their excellent heat-resistant properties, polyimides have been in wide use in various fields, ranging from the field of space and aeronautics and to the field of electronic communication. In recent years, however, the polymers are required, in addition to excellent heat-resistant properties, to have various characteristics suited for their particular uses.

For example, polyimides to be used as a base film for flexible printed circuit boards, as a carrier tape for TAB (tape automated bonding) or as a resin for laminated products are desired to have a low thermal expansion coefficient, a small dielectric constant and a low hygroscopicity. However, no polyimides have been known which satisfy these requirements to a satisfactory degree.

In order to obtain polyimides that satisfy the adove requirements, it is necessary to make the thermal expansion of polyimides quite low by making the main chain of polyimides as rigid as possible. A low thermal expansion can be readily attained when polyimides are synthesized by use of pyromellitic acid, which has the most rigid structure of all the existing compounds. In such a case, however, there is resulted an undesirably large polarization of imide groups, and hence it becomes impossible to attain low hygroscopicity. In theory, a low dielectric constant can be attained by introducing fluorine. However, the introduction of fluorine is disadvantageous in cost. In addition, it causes an undesirable lowering in the reactivity of resultant acid anhydrides.

SUMMARY OF THE INVENTION

It is an object of the present invention to provide novel acid anhydrides useful as a raw material for synthesizing polyimides having excellent properties, such as low thermal expansion, low dielectric constant, low hygroscopicity (water-resistance), and the like.

Other objects and advantages of the present invention will be apparent from the detailed description below.

The inventors have conducted intensive studies for the purpose of attaining the above objects and, as a result, accomplished the present invention.

DETAILED DESCRIPTION OF THE INVENTION

The present invention is, in one aspect, concerned with tetracarboxylic acid dianhydrides represented by the following formula [I A]:

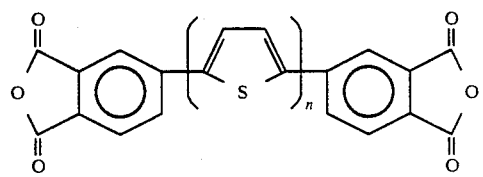

where n is an integer of 1 to 3.

The present invention is, in another aspect, concerned with tetracarboxylic acid dianhydrides represented by the following formula [I B]:

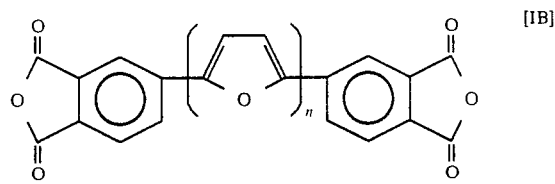

where n is an integer of 1 to 3.

The present invention will further be explained hereinbelow.

Using the technique of molecular designing, the inventors have designed various tetracarboxylic acid dianhydrides and evaluated polymers obtainable therefrom. As a result, it has been found that dianhydrides of aliphatic tetracarboxylic acids give polyimides having a low heat-resistance, and that thermal expansion of such polyimides could not be small because of the main chain. It has also been found that polyimides that wxhibit a low thermal expansion can be obtained by using pyromellitic acid, which has the most rigid structure of all the existing acid anhydrides. However, dielectric constant and hygroscopicity of sch polyimides are not small since the polarization of imide groups contained in the polymers is relatively large.

With the above results, the inventors have conceived that polyimides that exhibit a low thermal expansion may be obtained if a compound having the following formula [II]:

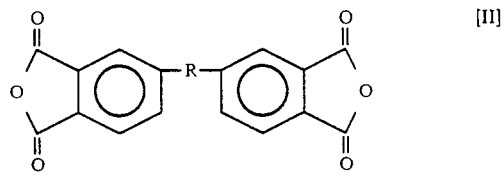

(where R is a divalent group) is used for the synthesis of polyimides, in particular, in the case where R is selected from a rigid, heat-resistant group. Such polyimides would slso have a low dielectric constant and a low hygroscopicity since the proportion of the polar imide rings contained in the polyimides can be small due to an increase in the molecular weight of the starting acid anhydrides. As a result of intensive studies based on the above conception, the inventors have found that a group having the following structures [III A] or [III B]:

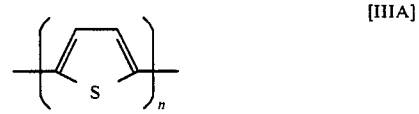

(where n is an integer of 1 to 3) can be suited for R in the above formula [II], and have invented the novel tetracarboxylic acid dianhydrides of the foregoing formula [I A] or [I B].

As examples of raw materials which can be used for the production of compounds represented by the formula [I A], there may be included bis-o-xylinothienyl, bis-o-xylinobithienyl and bis-o-xylinoterthienyl, which are represented by the following formula [IV A]:

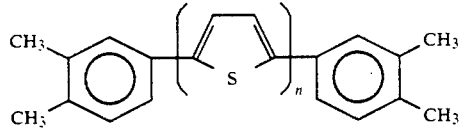
[IVA]

where n is an integer of 1 to 3.

These compounds can be obtained in accordance with the following reaction formula [V A]:

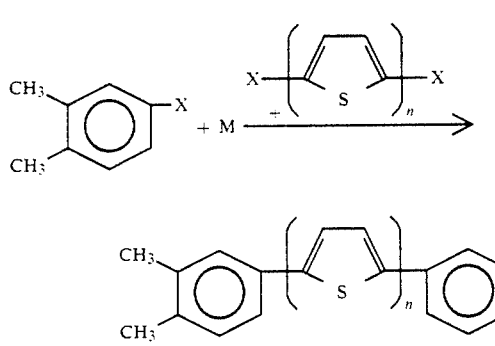
[VA]

where X is Br or I, n is an integer of 1 to 3, and M is metallic magnesium or metallic lithium.

To be more specific, 3-bromo-o-xylene or 3-iodo-o-xylene may be reacted with metallic magnesium or metallic lithium and then with a compound represented by the following formula:

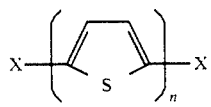

(where X is I or Br, and n is an integrer of 1 to 3) in ether or in an aprotic solvent, to give a compound represented by the formula [IV A].

The compounds represented by the formula [IV A] can also be produced by subjecting 3-bromo-o-xylene or 3-iodo-o-xylene to oxidative coupling with a compound represented by the following formula:

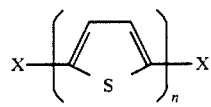

(where X is Br or I, and n is an integer of 1 to 3) in water or in a mixture of water and methanol in the presence of hydrogen peroxide and a catalyst selected from the group consisting of metallic palladium, an alloy of palladium and mercury, palladium chloride, and a mixture of palladium chloride and mercuric chloride, in accordance with the following reaction formula [VI A]:

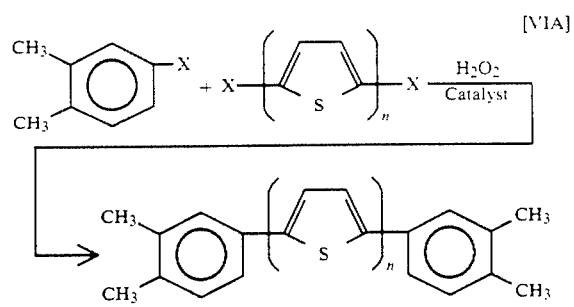
[VIA]

where X is Br or I, n is an integer of 1 to 3, and a catalyst is selected from the members mentioned hereinabove.

The compounds represented by the formula [IV A], i.e., bis-o-xylinothienyl, bis-o-xylynobithienyl and bis-o-xylinotertienyl, can be converted into dianhydrides of tetracarboxylic acids represented by the formula [I A] in accordance with the conventional oxidation and dehydrationring closure techniques. For example, the methyl groups can be oxidized according to the potassium permanganate method, the nitrate method, or the like. The cyclization to acid anhydrides can be effected according to the acetic anhydride method, the thermal dehydration method, or the like. It is also possible to directly form acid anhydrides by means of air oxidation using a vanadium pentoxide catalyst.

On the other hand, as examples of raw materials which can be used for the production of compounds represented by the formula [I B], there may be included bis-o-xylinofuryl, bis-o-xylinobifuryl and bis-o-xylinoterfuryl, which are represented by the following formula [IV B]:

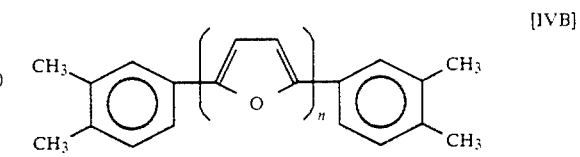
[IVB]

where n is an integer of 1 to 3.

These compounds can be obtained in accordance with the following reaction formula [V B]:

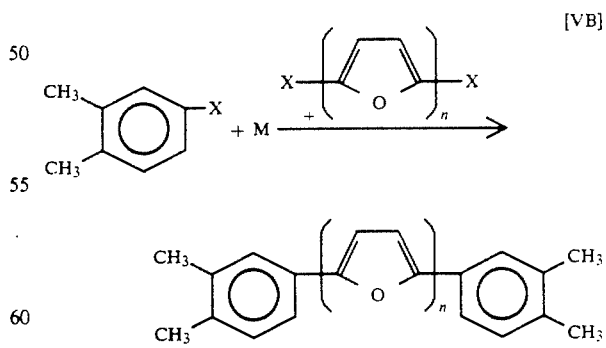
[VB]

where X is Br or I, n is an integre of 1 to 3, and M is metallic magnesium or metallic lithium.

To be more specific, 3-bromo-o-xylene or 3-iodo-o-xylene may be reacted with metallic magnesium or metallic lithium and then with a compound represented by the following formula:

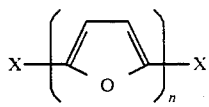

(where X is I or Br, and n is an integrer of 1 to 3) in ether or in an aprotic solvent, to give a compound represented by the formula [IV B].

The compounds represented by the formula [IV B] can also be produced by subjecting 3-bromo-o-xylene or 3-iodo-o-xylene to oxidative coupling with a compound represented by the following formula:

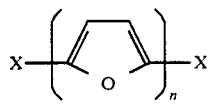

(where X is Br or I, and n is an integer of 1 to 3) in water or in a mixture of water and methanol in the presence of hydrogen peroxide and a catalyst selected from the group consisting of metallic palladium, an alloy of palladium and mercury, palladium chloride, and a mixture of palladium chloride and mercuric chloride, in accordance with the following reaction formula [VI B]:

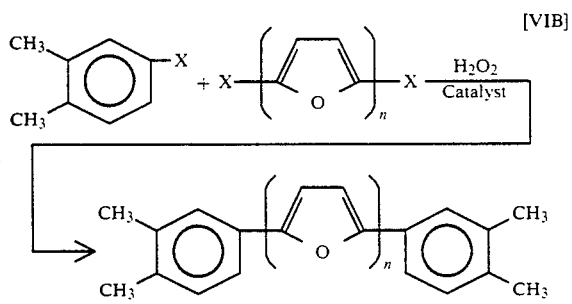

where X is Br or I, n is an integer of 1 to 3, and a catalyst is selected from the members mentioned hereinabove.

The compounds represented by the formula [IV B], i.e., bis-o-xylinofuryl, bis-o-xylynobifuryl and bis-o-xylinoterfuryl, can be converted into dianhydrides of tetracarboxylic acids represented by the formula [I B] in accordance with the conventional oxidation and dehydration-ring closure techniques. For example, the methyl groups can be oxidized according to the potassium permanganate method, the nitrate method, or the like. The cyclization to acid anhydrides can be effected according to the acetic anhydride method, the thermal dehydration method, or the like. It is also possible to directly form acid anhydrides by means of air oxidation using a vanadium pentoxide catalyst.

The present invention will be explained in further detail by way of examples. It should however be noted that the invention is by no means limited thereto.

EXAMPLE 1

Synthesis of 2,5-bis (3-o-xylino) thienyl

Into an Erlenmeyer flask were placed 51.1 g (220 mmol) of 3-iodo-o-xylene, 5.5 g (225 mmol) of metallic magnesium ribbon and 500 g of diethyl ether. After the resulting mixture had been stirred for 3 hours at room temperature under the atmosphere of nitrogen, the reaction vessel was cooled with ice, and a solution prepared by dissolving 33.6 g (100 mmol) of 2,5-diiodo-thienyl into 300 g of diethyl ether was added thereto. Subsequently, the resulting mixture was stirred for 2 hours under ice cooling and then heated and stirred under reflux for 1 hour. After the reaction, diethyl ether was distilled off, and the solid residue was purified by means of vacuum distillation using a glass tube oven, to give 2,5-bis (3-o-xylino) thienyl.

The thus obtained compound was identified as the desired thienyl compound by the molecular ion peak (m/e=292) in mass spectrometry and by elementary analysis, the results of which were in good agreement with the theoretical values as set forth below.

Elementary Analysis: Calculated: C, 82.54, H, 6.89. Measured: C, 82.20, H, 6.80.

EXAMPLE 2

Synthesis of 2,5-bis (3-o-xylino) thienyl

Into an Erlenmeyer flask were placed 51.1 g (220 mmol) of 3-iodo-o-xylene, 55.0 g (450 mmol) of a 28% aqueous 28% hydrogen peroxide solution, 0.9 g (5 mmol) of $PdCl_2$, 33.6 g (100 mmol) of 2,5-diiodothienyl and 400 g of methanol. The resulting mixture was heated and stirred under reflux for 8 hours, and the metal catalyst was removed by means of filtration. The filtrate was then distilled off, and the solid residue was purified by means of vacuum distillation using a glass tube oven, to give 2,5-bis (3-o-xylino) thienyl.

The thus obtained compound was identified in the same manner as in Example 1.

EXAMPLE 3

Synthesis of bis (3-phthalic anhydrido)-2,5-thienyl

Into a three-necked flask were charged 8.1 g (62 mmol) of 2,5-bis (3-o-xylino) thienyl, 550 ml of pyridine and 200 ml of distilled water, and the resulting mixture was heated to 100° C. To this was added by portions 48.9 g (310 mmol) of potassium permanganate, and the resulting mixture was stirred for 3 hours. After the reaction, the reaction mixture was filtered, and the solvents contained in the filtrate were distilled off to give a solid residue.

The solid residue was added to 700 g of a 6 weight % aqueous sodium hydroxide solution, and the resulting mixture was heated to 100° C. To this was gradually added 58.8 g of potassium permanganate, and the resulting mixture was stirred for 2 hours to allow the reaction to proceed. After the reaction, ethanol was added to the reaction mixture to decompose the remaining potassium permanganate, and the resulting mixture was filtered. The filtrate was cooled and then added with hydrochloric acid to allow the product to precipitate. After being dried, the precipitate was thermally treated at 1 Torr at 200° C. and then purified by means of sublimation, to obtain the desired bis (3-phthalic anhydrido)-2,5-thienyl.

The thus obtained compound was identified as the desired thienyl compound by the molecular ion peak (m/e=376) in mass spectrometry and by elementary analysis, the results of which were in good agreement with the theoretical values as set forth below.

Elementary Analysis: Calculated: C, 63.83, H, 2.14. Measured: C, 63.75, H, 2.20.

EXAMPLE 4

Synthesis of bis-5,5'-[(3-o-xylino)-2-thienyl]

Into an Erlenmeyer flask were placed 51.1 g (220 mmol) of 3-iodo-o-xylene, 5.5 g (225 mmol) of metallic magnesium ribbon and 400 g of diethyl ether. After the resulting mixture had been stirred for 3 hours at room temperature under the atmosphere of nitrogen, the reaction vessel was cooled with ice, and a solution prepared by dissolving 41.8 g (100 mmol) of 5,5'-diiodo-2,2'-bithienyl into 300 g of diethyl ether was added thereto. Subsequently, the resulting mixture was stirred for 2 hours under ice cooling and then heated and stirred under reflux for 1 hour. After the reaction, diethyl ether was distilled off, and the solid residue was purified by means of vacuum distillation using a glass tube oven, to give 5,5'-[(3-o-xylino)-2-thienyl].

The thus obtained compound was identified as the desired thienyl compound by the molecular ion peak (m/e=375) in mass spectrometry and by elementary analysis, the results of which were in good agreement with the theoretical values as set forth below.

Elementary Analysis: Calculated: C, 76.96, H, 5.92. Measured: C, 76.80, H, 6.00.

EXAMPLE 5

Synthesis of bis-5,5'-[(3-phthalic anhydrido)-2-thienyl]

Into a three-necked flask were charged 23.3 g (62 mmol) of 5,5'-[(3-o-xylino)-2-thienyl, 550 ml of pyridine and 200 ml of distilled water, and the resulting mixture was heated to 100° C. To this was added by portions 48.9 g (310 mmol) of potassium permanganate, and the resulting mixture was stirred for 3 hours. After the reaction, the reaction mixture was filtered, and the solvents contained in the filtrate were distilled off to give a solid residue.

The solid residue was added to 750 g of a 6 weight % aqueous sodium hydroxide solution, and the resulting mixture was heated to 100° C. To this was gradually added 60 g of potassium permanganate, and the resulting mixture was stirred for 2 hours to allow the reaction to proceed. After the reaction, ethanol was added to the reaction mixture to decompose the remaining potassium permanganate, and the resulting mixture was filtered. The filtrate was cooled and then added with hydrochloric acid to allow the product to precipitate. After being dried, the precipitate was thermally treated at 1 Torr at 200° C. and then purified by means of sublimation, to obtain to desired 5,5'-[(3-phthalic anhydrido)-2-thienyl].

The thus obtained compound was identified as the desired thienyl compound by the molecular ion peak (m/e=458) in mass spectrometry and by elementary analysis, the results of which were in good agreement with the theoretical values as set forth below.

Elementary Analysis: Calculated: C, 62.88, H, 2.20. Measured: C, 62.90, H, 2.24.

EXAMPLE 6

Synthesis of bis-2,5''-(3-o-xylino)-5,2':5',2''-terthienyl

Into an Erlenmeyer flask were placed 51.1 g (220 mmol) of 3-iodo-o-xylene, 5.5 g (225 mmol) of metallic magnesium ribbon and 500 g of diethyl ether. After the resulting mixture had been stirred for 3 hours at room temperature under the atmosphere of nitrogen, the reaction vessel was cooled with ice, and a solution prepared by dissolving 5.0 g (100 mmol) of 2,5''-diiodo-5,2':5',2''-terthienyl into 300 g of diethyl ether was added thereto. Subsequently, the resulting mixture was stirred for 2 hours under ice cooling and then heated and stirred under reflux for 1 hour. After the reaction, diethyl ether was distilled off, and the solid residue was purified by means of vacuum distillation using a glass tube oven, to give bis-2,5''-(3-o-xylino)-5,2':5',2''-terthienyl.

The thus obtained compound was identified as the desired terthieyl compound by the molecular ion peak (m/e=457) in mass spectrometry and by elementary analysis, the results of which were in good agreement with the theoretical values as set forth below.

Elementary Analysis: Calculated: C, 73.64, H, 5.30. Measured: C, 73.70, H, 5.20.

EXAMPLE 7

Synthesis of bis-2,5''-(3-phthalic anhydrido)-5,2':5'2''-terthinenyl

Into a three-necked flask were charged 28.3 g (62 mmol) of 5,5''-(3-o-xylino)-5,2':5'2''-terthinenyl, 550 ml of pyridine and 200 ml of distilled water, and the resulting mixture was heated to 100° C. To this was added by portions 48.9 g (310 mmol) of potassium permanganate, and the resulting mixture was stirred for 3 hours. After the reaction, the reaction mixture was filtered, and the solvents contained in the filtrate were distilled off to give a solid residue.

The residue was added to 750 g of a 6 weight % aqueous sodium hydroxide solution, and the resulting mixture was heated to 100° C. To this was gradually added 60 g of potassium permanganate, and the resulting mixture was stirred for 2 hours to allow the reaction to proceed. After the reaction, ethanol was added to the reaction mixture to decompose the remaining potassium permanganate, and the resulting mixture was filtered. The filtrate was cooled and then added with hydrochloric acid to allow the product to precipitate. After being dried, the precipitate was thermally treated at 1 Torr at 200° C. and then purified by means of sublimation, to obtain to desired 2,5''-(3-phthalic anhydrido)-5,2':5'2''-terthinenyl.

The thus obtained compound was identified as the desired terthienyl compound by the molecular ion peak (m/e=541) in mass spectrometry and by elementary analysis, the results of which were in good agreement with the theoretical values as set forth below.

Elementary Analysis: Calculated: C, 62.21, H, 2.24. Measured: C, 62.30, H, 2.40.

REFERENCE EXAMPLE 1

PRODUCTION OF POLYIMIDE COPOLYMER FILM

Into a three-necked flask were placed 12.4 g (115 mmol) of p-phenylenediamine and 200 g of dimethylformamide (hereinafter referred to as DMF). Then, 41.4 g (110 mmol) of bis (3-phthalic anhydrido)-2,5-thienyl synthesized in Example 3 was gradually added thereto, and the resulting mixture was stirred for 30 minutes. Thereafter, an 8 weight % DMF solution of 5 mol of bis(3-phthalic anhydrido)-2,5-thienyl was gradually added thereto, to obtain a polyamic acid solution.

The polyamic acid solution was admixed with an excess of acetic anhydride and a catalytic amount of a tertiary amine. The resulting mixture was cast on a glass plate and dried at ca. 80° C. for ca. 90 seconds, and the polyamic acid film formed was peeled off the glass plate. The film was fixed on a supporting frame, heated at ca. 100° C. for ca. 90 seconds and then stretched.

Thereafter, the stretched film was heated at ca. 250° C. for ca. 30 seconds, at ca. 300° C. for ca. 30 seconds, at ca. 400° C. for ca. 30 seconds and then at ca. 450° C. for ca. 2 minutes, to obtain a polyimide copolymer film having a thickness of ca. 25 μm.

The physical properties of the thus obtained polyimide copolymer film are shown in Table 1.

COMPARATIVE REFERENCE EXAMPLE 1

PRODUCTION OF POLYIMIDE COPOLYMER FILM

Into a three-necked flask were placed 26.0 g (130 mmol) of diamino diphenyl ether and 200 g of DMF. While stirring, 27.0 g (124 mmol) of pyromellitic acid dianhydride was gradually added thereto. Thereafter, a 7 weight DMF solution of 6 mol of pyromellitic acid dianhydride was gradually added thereto, to obtain a polyamic acid solution.

A polyimide copolymer film was prepared from the polyamic acid solution in the same manner as in Reference Example 1.

The physical properties of the thus obtained polymide copolymer film are also shown in Table 1.

TABLE 1

|  | Reference Example 1 | Comparative Reference Example |
|---|---|---|
| Thermal Expansion Coefficient (1) ($\times 10^{-5}$ °C.$^{-1}$) | 1.2 | 3.7 |
| Dielectric Constant (2) | 2.7 | 3.0 |
| Water Absorption (3) (%) | 0.5 | 3.2 |

[Notes]
(1): Measured at 100 to 200° C. by thermal mechanical analysis.
(2): Measured according to ASTM D-150
(3): Measured according to ASTM D-570

EXAMPLE 8

Synthesis of 2,5-bis (3-o-xylino) furyl

Into an Erlenmeyer flask were placed 51.1 g (220 mmol) of 3-iodo-o-xylene, 5.5 g (225 mmol) of metallic magnesium ribbon and 500 g of diethyl ether. After the resulting mixture had been stirred for 3 hours at room temperature under the atmosphere of nitrogen, the reaction vessel was cooled with ice, and a solution prepared by dissolving 27.6 g (100 mmol) of 2,5-diiodo-furyl into 300 g of diethyl ether was added thereto. Subsequently, the resulting mixture was stirred for 2 hours under ice cooling and then heated and stirred under reflux for 1 hour. After the reaction, diethyl ether was distilled off, and the solid residue was purified by means of vacuum distillation using a glass tube oven, to give 2,5-bis (3-o-xylino) furyl.

The thus obtained compound was identified as the desired thienyl compound by the molecular ion peak (m/e=276) in mass spectrometry and by elementary analysis, the results of which were in good agreement with the theoretical values as set forth below.

Elementary Analysis: Calculated: C, 86.92, H, 7.29. Measured: C, 86.80, H, 7.40.

EXAMPLE 9

Synthesis of 2,5-bis (3-o-xylino) furyl

Into an Erlenmeyer flask were placed 51.1 g (220 mmol) of 3-iodo-o-xylene, 55.0 g (450 mmol) of a 28% aqueous 28% hydrogen peroxide solution, 0.9 g (5 mmol) of PdCl$_2$, 32.0 g (100 mmol) of 2,5-diiodofuryl and 400 g of methanol. The resulting mixture was heated and stirred under reflux for 8 hours, and the metal catalyst was removed by means of filtration. The filtrate was then distilled off, and the solid residue was purified by means of vacuum distillation using a glass tube oven, to give 2,5-bis (3-o-xylino) furyl.

The thus obtained compound was identified in the same manner as in Example 8.

EXAMPLE 10

Synthesis of bis (3-phthalic anhydrido)-2,5-furyl

Into a three-necked flask were charged 17.1 g (62 mmol) of 2,5-bis (3-o-xylino) furyl, 550 ml of pyridine and 200 ml of distilled water, and the resulting mixture was heated to 100° C. To this was added by portions 48.9 g (310 mmol) of potassium permanganate, and the resulting mixture was stirred for 3 hours. After the reaction, the reaction mixture was filtered, and the solvents contained in the filtrate were distilled off to give a solid residue.

The solid residue was added to 700 g of a 6 weight % aqueous sodium hydroxide solution, and the resulting mixture was heated to 100° C. To this was gradually added 58.8 g of potassium permanganate, and the resulting mixture was stirred for 2 hours to allow the reaction to proceed. After the reaction, ethanol was added to the reaction mixture to decompose the remaining potassium permanganate, and the resulting mixture was filtered. The filtrate was cooled and then added with hydrochloric acid to allow the product to precipitate. After being dried, the precipitate was thermally treated at 1 Torr at 200° C. and then purified by means of sublimation, to obtain the desired bis (3-phthalic anhydrido)-2,5-furyl.

The thus obtained compound was identified as the desired thienyl compound by the molecular ion peak (m/e=360) in mass spectrometry and by elementary analysis, the results of which were in good agreement with the theoretical values as set forth below.

Elementary Analysis: Calculated: C, 66.68, H, 2.24. Measured: C, 66.80, H, 2.20.

EXAMPLE 11

Synthesis of bis-5,5'-[(3-o-xylino)-2-furyl]

Into an Erlenmeyer flask were placed 51.1 g (220 mmol) of 3-iodo-o-xylene, 5.5 g (225 mmol) of metallic magnesium ribbon and 400 g of diethyl ether. After the resulting mixture had been stirred for 3 hours at room temperature under the atmosphere of nitrogen, the reaction vessel was cooled with ice, and a solution prepared by dissolving 38.6 g (100 mmol) of 5,5'-diiodo-2,2'-furyl into 300 g of diethyl ether was added thereto. Subsequently, the resulting mixture was stirred for 2 hours under ice cooling and then heated and stirred under reflux for 1 hour. After the reaction, diethyl ether was distilled off, and the solid residue was purified by means of vacuum distillation using a glass tube oven, to give 5,5'-[(3-o-xylino)-2-furyl].

The thus obtained compound was identified as the desired thienyl compound by the molecular ion peak (m/e=342) in mass spectrometry and by elementary analysis, the results of which were in good agreement with the theoretical values as set forth below.

Elementary Analysis: Calculated: C, 84.18, H, 6.48. Measured: C, 84.22, H, 6.40.

EXAMPLE 12

Synthesis of bis-5,5'-[(3-phthalic anhydrido)-2-furyl]

Into a three-necked flask were charged 21.2 g (62 mmol) of 5,5'-[(3-o-xylino)-2-furyl, 550 ml of pyridine and 200 ml of distilled water, and the resulting mixture was heated to 100° C. To this was added by portions 48.9 g (310 mmol) of potassium permanganate, and the resulting mixture was stirred for 3 hours. After the reaction, the reaction mixture was filtered, and the solvents contained in the filtrate were distilled off to give a solid residue.

The solid residue was added to 750 g of a 6 weight % aqueous sodium hydroxide solution, and the resulting mixture was heated to 100° C. To this was gradually added 60 g of potassium permanganate, and the resulting mixture was stirred for 2 hours to allow the reaction to proceed. After the reaction, ethanol was added to the reaction mixture to decompose the remaining potassium permanganate, and the resulting mixture was filtered. The filtrate was cooled and then added with hydrochloric acid to allow the product to precipitate. After being dried, the precipitate was thermally treated at 1 Torr at 200° C. and then purified by means of sublimation, to obtain to desired 5,5'-[(3-phthalic anhydrido)-2-furyl].

The thus obtained compound was identified as the desired thienyl compound by the molecular ion peak (m/e=426) in mass spectrometry and by elementary analysis, the results of which were in good agreement with the theoretical values as set forth below.

Elementary Analysis: Calculated: C, 67.61, H, 2.36. Measured: C, 67.70, H, 2.50.

EXAMPLE 13

Synthesis of bis-2,5''-(3-o-xylino)-5,2':5',2''-furyl

Into an Erlenmeyer flask were placed 51.1 g (220 mmol) of 3-iodo-o-xylene, 5.5 g (225 mmol) of metallic magnesium ribbon and 500 g of diethyl ether. After the resulting mixture had been stirred for 3 hours at room temperature under the atmosphere of nitrogen, the reaction vessel was cooled with ice, and a solution prepared by dissolving 45.2 g (100 mmol) of 2,5''-diiodo-5,2':5',2''-terfuryl into 300 g of diethyl ether was added thereto. Subsequently, the resulting mixture was stirred for 2 hours under ice cooling and then heated and stirred under reflux for 1 hour. After the reaction, diethyl ether was distilled off, and the solid residue was purified by means of vacuum distillation using a glass tube oven, to give bis-2,5''-(3-o-xylino)-5,2':5',2''-terfuryl.

The thus obtained compound was identified as the desired terthieyl compound by the molecular ion peak (m/e= 409) in mass spectrometry and by elementary analysis, the results of which were in good agreement with the theoretical values as set forth below.

Elementary Analysis: Calculated: C, 82.32, H, 5.92. Measured: C, 82.40, H, 6.02.

EXAMPLE 14

Synthesis of bis-2,5''-(3-phthalic anhydrido)-5,2':5'2''-terfuryl

Into a three-necked flask were charged 25.4 g (62 mmol) of 5,5''-(3-o-xylino)-5,2':5'2''-terfuryl, 550 ml of pyridine and 200 ml of distilled water, and the resulting mixture was heated to 100° C. To this was added by portions 48.9 g (310 mmol) of potassium permanganate, and the resulting mixture was stirred for 3 hours. After the reaction, the reaction mixture was filtered, and the solvents contained in the filtrate were distilled off to give a solid residue.

The residue was added to 750 g of a 6 weight % aqueous sodium hydroxide solution, and the resulting mixture was heated to 100° C. To this was gradually added 60 g of potassium permanganate, and the resulting mixture was stirred for 2 hours to allow the reaction to proceed. After the reaction, ethanol was added to the reaction mixture to decompose the remaining potassium permanganate, and the resulting mixture was filtered. The filtrate was cooled and then added with hydrochloric acid to allow the product to precipitate. After being dried, the precipitate was thermally treated at 1 Torr at 200° C. and then purified by means of sublimation, to obtain to desired 2,5''-(3-phthalic anhydrido)-5,2':5'2''-terfuryl.

The thus obtained compound was identified as the desired terthienyl compound by the molecular ion peak (m/e=492) in mass spectrometry and by elementary analysis, the results of which were in good agreement with the theoretical values as set forth below.

Elementary Analysis: Calculated: C, 68.30, H, 2.46. Measured: C, 68.25, H, 2.50.

REFERENCE EXAMPLE 2

Production of Polyimide Copolymer Film

Into a three-necked flask were placed 21.6 g (200 mmol) of p-phenylenediamine and 360 g of dimethylformamide (hereinafter referred to as DMF). Then, 68.5 g (190 mmol) of bis (3-phthalic anhydrido)-2,5-furyl synthesized in Example 10 was gradually added thereto, and the resulting mixture was stirred for 30 minutes. Thereafter, an 8 weight % DMF solution of 10 mol of bis(3-phthalic anhydrido)-2,5-furyl was gradually added thereto, to obtain a polyamic acid solution.

The polyamic acid solution was admixed with an excess of acetic anhydride and a catalytic amount of a tertiary amine. The resulting mixture was cast on a glass plate and dried at ca. 80° C. for ca. 90 seconds, and the polyamic acid film formed was peeled off the glass plate. The film was fixed on a supporting frame, heated at ca. 100° C. for ca. 90 seconds and then stretched. Thereafter, the stretched film was heated at ca. 250° C. for ca. 30 seconds, at ca. 300° C. for ca. 30 seconds, at ca. 400° C. for ca. 30 seconds and then at ca. 450° C. for ca. 2 minutes, to obtain a polyimide copolymer film having a thickness of ca. 25 μm.

The physical properties of the thus obtained polyimide copolymer film are shown in Table 2.

The results of Comparative Reference Example 1 are also given in Table 2.

TABLE 2

|  | Reference Example 2 | Comparative Reference Example 1 |
| --- | --- | --- |
| Thermal Expansion Coefficient (1) ($\times 10^{-5}$ °C.$^{-1}$) | 1.2 | 3.7 |
| Dielectric Constant (2) | 2.7 | 3.0 |
| Water Absorption (3) (%) | 0.5 | 3.2 |

[Notes]
(1): Measured at 100 to 200° C. by thermal mechanical analysis.
(2): Measured according to ASTM D-150
(3): Measured according to ASTM D-570

As described hereinabove, the invention provides tetracarboxylic acid dianhydrides which are capable of providing polyimides having low thermal expansion, low dielectric constant and low hygroscopicity.
What is claimed is:
1. Tetracarboxylic acid dianhydrides represented by the following formula [I A]:
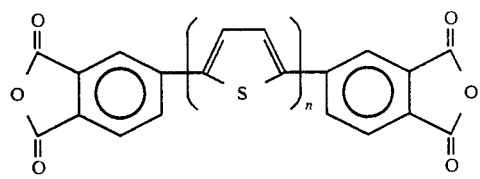
where n is an integer of 1 to 3.
2. Tetracarboxylic acid dianhydrides represented by the following formula [I B]:
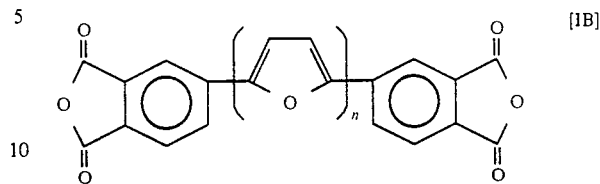
where n is an integer of 1 to 3.
* * * * *